United States Patent [19]
Henrick et al.

[11] 3,960,907
[45] June 1, 1976

[54] ESTERS OF CYCLOPROPYL SUBSTITUTED CARBOXYLIC ACIDS

[75] Inventors: Clive A. Henrick; Gerardus B. Staal, both of Palo Alto, Calif.

[73] Assignee: Zoecon Corporation, Palo Alto, Calif.

[22] Filed: July 17, 1974

[21] Appl. No.: 489,207

[52] U.S. Cl. ..................... 260/410.9 R; 260/468 H
[51] Int. Cl.$^2$ .......................................... C11C 3/02
[58] Field of Search ............... 260/410.9 R, 468 H

[56] References Cited
UNITED STATES PATENTS
3,578,685   5/1971   Archer ........................... 260/468 H

OTHER PUBLICATIONS

Morrison and Boyd "Organic Chemistry" 3rd Ed. 1973 p. 602.

*Primary Examiner*—Patrick P. Garvin
*Assistant Examiner*—John F. Niebling
*Attorney, Agent, or Firm*—Donald W. Erickson

[57] ABSTRACT

Esters of cyclopropyl substituted carboxylic acids, syntheses thereof, compositions thereof, and use for the control of mites and ticks.

10 Claims, No Drawings

ESTERS OF CYCLOPROPYL SUBSTITUTED CARBOXYLIC ACIDS

This invention relates to novel compounds, synthesis thereof, compositions thereof, and the control of mites.

The compounds of the present invention are effective for the control of mites and especially spider mites. Spider mites are plant feeders and cause serious damage to orchard trees, field crops, greenhouse plants and other vegetation. They feed on the foliage and fruit of plants and trees and attack a variety of plants and trees due to their wide distribution. Spider mites of the family Tetranychidae, such as *Tetranychus urticae, Tetranychus canadensis, Tetranychus cinnabarinus, Tetranychus pacificus, Bryobia praetiosa, Oligonychus pratensis, Oligonychus ilicis, Panonychus citri, Panonychus ulmi*, and similar relted species, are of particular biological interest and economic importance. Other mites are those of the family Tarsonemidae, such as *Steneotarsonemus pallidus*.

Compounds of the present invention of the following formula I are effective control agents for mites

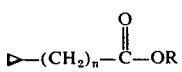 (I)

wherein *n* is an even integer of 6 to 14 and R is alkyl of one to 16 carbon atoms, with the proviso that each compound of formula I contains at least 15 but not more than 26 carbon atoms in the molecule.

Hereinafter, each of R and *n* is as defined above unless otherwise specified.

The compounds of formula I are applied to the mite during the egg, larval or nymphal stages in view of their effect in causing causing inhibition of egg hatching, abnormal development leading to death, inability to pass from one stage to the next, or inability to reproduce. Some of the compounds also exhibit a residual ovicidal effect. A compound of formula I can be applied at concentration levels of the order of 0.001% to 1%, usually 0.01% to 0.1% by weight. Suitable carrier substances include liquid or solid inert carriers, such as water, acetone, xylene, mineral or vegetable oils, talc, vermiculite, and silica. Treatment of mites in accordance with the present invention can be accomplished by spraying, dusting, or otherwise contacting the mites and/or their eggs or larvae directly or indirectly. Generally, a concentration of less than 25% of active compound in the formulation is used depending on the type of application apparatus. The formulations can include emulsifying agents and wetting agents to assist in the application and effectiveness of the active ingredient.

The esters of Formula I can be prepared by reacting the appropriate alcohol ROH with at least one mole of an acid of the formula

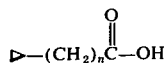

in the presence of an acid catalyst and with heating. The reaction can be carried out in the absence of a solvent; however, use of a solvent inert to the reaction, such as an ether, dichloromethane, chloroform, or hydrocarbon solvent, is preferred. Water may be removed by azeotropic distillation, if desired.

Alternatively, the appropriate acid halide

may be reacted with the alcohol ROH in the presence of pyridine and at either room temperature or, when the alcohol is sensitive, at from about −10° to about 0°C.

The acids of the formula

can be prepared by conventional methods known in the art. In one method, cyclopropyl bromide is treated first with lithium and then with cuprous iodide to form the intermediate

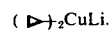

This intermediate is reacted with a halide-substituted ester of the formula Halide

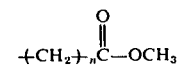

to yield

which is then hydrolyzed to the free acid. In another method, an unsaturated ester of the formula

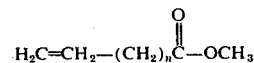

is reacted with methylene iodide in the presence of zinc-copper couple to yield

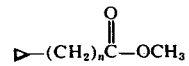

which is then hydrolyzed to the free acid. Alternatively, the method of U.S. Pat. No. 3,578,685 using cyclopropanecarboxylic acid chloride and 1-morpholinocyclohexene as starting materials is employed. The preparation of the starting materials is shown in copending Ser. No. 461,189, filed Apr. 12, 1974, the disclosure of which is hereby incorporated by reference.

The term "alkyl", as used herein, refers to a straight or branched chain saturated aliphatic hydrocarbon group of one to sixteen carbon atoms, e.g. methyl, ethyl, propyl, octyl, 2-methyloctyl, undecyl, pentadecyl, and the like.

The term "halide" as used herein refers to chloride, bromide, or iodide.

The esters of the present invention can be used alone or in an inert carrier substance for the control of mites (Acarina) or can be used in mixture with pesticides and/or juvenile hormone analogs known in the art in order to obtain a broader spectrum of activity. Suitable insecticides include Baygon, Captan, Sevin, Ciodrin, Systox, Diazinon, Vapona, Galecron, Cygon, Dimethrin Dursban, Malathion, and Parathion. Typical juvenile hormone analogs which can be used in mixture with the compound of the present invention are described in U.S. Pat. Nos. 3,752,843 and 3,755,411.

The esters of the present invention are useful for the control of mites and ticks which are ectoparasitic on animals and birds. The compounds can be applied in either solution or in powder (dust) form in a conventional manner.

The following examples are provided to illustrate the synthesis of the esters of the present invention and the practice of the present invention. Temperature is in degrees Centigrade. All boiling points were measured by short path distillation.

EXAMPLE 1

A. A mixture of 12.7 ml. methylene diiodide and 12.2 g. zinc-copper couple in 75 ml. ether is heated under nitrogen for several hours and then 10.0 g. methyl 10-undecenoate in 10 ml. ether is added dropwise. The reaction mixture is refluxed for 7 hours, stirred overnight at room temperature, refluxed for 8 hours, stirred for 5 days at room temperature and then refluxed for 8 hours.

Excess zinc reagents are decomposed by the dropwise addition of saturated aqueous ammonium chloride solution until a black precipitate is formed. The mixture is filtered through celite and the solid material is washed with ether. The combined ethereal phases are washed, in turn, with 2N sulfuric acid (3 × 50 ml.), 10% aqueous sodium carbonate (4 × 100 ml.), water (2 × 50 ml.) and saturated aqueous sodium chloride (1 × 50 ml.). The ethereal phase is then dried over calcium sulfate, filtered through activity III neutral alumina, concentrated by evaporation, and distilled to yield 7.44 g. of methyl 9-cyclopropylnonanoate, boiling point 107° at 1.0 mm. The product is purified by spinning band distillation.

B. A mixture of 1.20 g. of methyl 9-cyclopropylnonanoate and 0.30 g. of sodium hydroxide in 12 ml. of a 2:1 mixture of methanol and water is stirred at room temperature for 4 hours. The mixture is acidified with 2N sulfuric acid to a pH of 1 and then extracted with ether (3 × 100 ml.). The combined ethereal phases are washed with water (1 × 50 ml.) and saturated aqueous sodium chloride (2 × 50 ml.) dried over calcium sulfate and the solvent removed to give 0.85 g. of 9-cyclopropylnonanoic acid.

C. A mixture of 0.85 g. of 9-cyclopropylnonanoic acid, 0.45 ml. of thionyl chloride (density 1.656) and 0.10 ml. of dimethylformamide (density 0.945) in 10 ml. ether is stirred overnight at room temperature. The upper layer of the reaction mixture is then separated and the solvent removed by evaporation to yield 9-cyclopropylnonanoyl chloride to which is added at 0° under nitrogen 0.474 g. of 1-octanol and 40 ml. of ether. To this mixture is added dropwise 0.52 ml. of pyridine (density 0.98). The reaction mixture is then stirred ½ hour at 0° and overnight at room temperature. An additional 0.20 g. of 1-octanol is then added and the reaction mixture is stirred for one day. The mixture is filtered, 3 equivalents of water are added and the mixture is stirred for one hour. Ether is added to dilute the reaction mixture which is washed in turn with 2N sulfuric acid (2 × 50 ml.), 10% aqueous sodium carbonate (2 × 50 ml.), water (2 × 50 ml.) saturated aqueous copper sulfate, water (2 × 50 ml.) and saturated aqueous sodium chloride (1 × 50 ml.). The solution is then dried over calcium sulfate and the solvent removed by evaporation to yield 1.14 g. of octyl 9-cyclopropylnonanoate which is purified by preparative thin layer chromotography (15% ether/hexane solvent).

EXAMPLE 2

A mixture of 49 g. of 11-bromoundecanoic acid, 500 ml. anhydrous dimethyl formamide, 27.5 g. anhydrous potassium carbonate and 79 g. methyl iodide is heated at 55° for 8 hours, then cooled and allowed to sit at room temperature for 10 days. The mixture is then filtered and to the filtrate is added ether (250 ml.), pentane (250 ml.) and water (1000 ml.). The organic layer is separated and washed in turn with water (2 × 150 ml.), aqueous saturated sodium chloride (1 × 100 ml.), dried over calcium sulfate and the solvent removed by evaporation to yield 45.56 g of product which is 27% methyl 11-bromoundecanoate and 53% methyl 11-iodoundecanoate.

Using the procedure of Example 2 with the acids of column I, the esters of column II along with varying amounts of the corresponding iodo esters are prepared.

I 7-chloroheptanoic acid
7-bromoheptanoic acid
9-chlorononanoic acid
9-bromononanoic acid
11-chloroundecanoic acid
13-bromotridecanoic acid
15-chloropentadecanoic acid

II methyl 7-chloroheptanoate
methyl 7-iodoheptanoate
methyl 7-bromoheptanoate
methyl 9-chlorononanoate
methyl 9-iodononanoate
methyl 9-bromononanoate
methyl 11-chloroundecanoate
methyl 11-iodoundecanoate
methyl 13-bromotridecanoate
methyl 13-iodotridecanoate
methyl 15-chloropentadecanoate
methyl 15-iodopentadecanoate

EXAMPLE 3

To a mixture of 2.6 g. of 1% sodium-lithium metal and 120 ml. of anhydrous ether at −15° under argon is slowly added over one hour 27.5 g. of cyclopropyl bromide. The mixture is stirred until the last pieces of lithium disappear and then is kept at −10° overnight. This mixture is then added, at −20°, to a mixture of 14.4 g. cuprous iodide and 120 ml. tetrahydrofuran. To this mixture is added, dropwise at −20° 15 g. of methyl 11-iodoundecanoate in 5 ml. of tetrahydrofuran. The mixture is then stirred at −20° for 1.5 hours and at 0° for 0.5 hours. Saturated aqueous ammonium chloride solution (100 ml.) is added dropwise with stirring at −20° and then the mixture is concentrated to about ½ volume by evaporation of the solvent. To the concentrated solution is added 200 ml. hexane, the mixture is filtered and the residue is washed with 200 ml. ether.

The organic layer is separated and washed in turn with water (2 × 100 ml.), saturated aqueous sodium chloride (1 × 100 ml.) and then dried over calcium sulfate. The solvent is removed by evaportion to yield 10.60 g. methyl 11-cyclopropylundecanoate, b.p. 124° at 0.1 mm.

Using the procedure of Example 3 with the esters of column II, the esters of column III are prepared.

III methyl 7-cyclopropylheptanoate
methyl 9-cyclopropylnonanoate
methyl 11-cyclopropylundecanoate
methyl 13-cyclopropyltridecanoate
methyl 15-cyclopropylpentadecanoate

EXAMPLE 4

A. A mixture of 5.76 g. methyl 11-cyclopropylundecanoate, 16 ml. methanol, 16 ml. ethanol, 8 ml. water and 1.25 g. sodium hydroxide is boiled for 1.5 hours and then cooled to yield a solid white mass to which is added 200 ml. water and 30 ml. 3N sulfuric acid. The mixture is concentrated by evaporation, 140 ml. ethyl acetate is added and the mixture is stirred overnight. The organic phase is separated and washed in turn with water (2 × 60 ml.) and saturated aqueous sodium chloride, dried over calcium sulfate and the solvent removed to yield 6.10 g. solid 11-cyclopropylundecanoic acid.

B. To a mixture of 3.5 g. 11-cyclopropylundecanoic acid, 105 ml. anhydrous ether, and 1.7 ml. thionyl chloride at 24° is added 0.3 ml. of dimethylformamide. The mixture is stirred for 3.5 hours and then the upper layer is separated and the solvent and volatile materials are removed to yield 3.38 g. 11-cyclopropylundecanoyl chloride.

C. To 60 ml. anhydrous ether and 1.69 g. 11-cyclopropylundecanoyl chloride is added 0.70 g. 1-hexanol. The mixture is cooled to 0° and 0.8 ml. pyridine is added. The solution is stirred at room temperature for 2 days. The product is worked-up using the procedure of Example 1C to yield 1.78 g. of hexyl 11-cyclopropylundecanoate.

Following the procedure of Example 4 using the esters of Column III and ethanol, propanol, butanol, pentanol, hexanol, heptanol, octanol, nonanol, decanol, undecanol, dedecanol, tridecanol, tetradecanol, pentadecanol, and hexadecanol yields esters of this invention as exemplified by those of column IV.

IV octyl 7-cyclopropylheptanoate
hexyl 9-cyclopropylnonanoate
butyl 11-cyclopropylundecanoate
ethyl 13-cyclopropyltridecanoate
dodecyl 7-cyclopropylheptanoate
decyl 9-cyclopropylnonanoate
octyl 11-cyclopropylundecanoate
hexyl 13-cyclopropyltridecanoate
butyl 15-cyclopropylpentadecanoate
tridecyl 7-cyclopropylheptanoate
nonyl 11-cyclopropylundecanoate
nonyl 7-cyclopropylheptanoate
heptyl 9-cyclopropylnonanoate
pentyl 11-cyclopropylundecanoate
propyl 13-cyclopropyltridecanoate
pentyl 7-cyclopropylheptanoate
hexyl 15-cycloproylpentadecanoate
decyl 11-cyclopropylundecanoate
tetradecyl 7-cyclopropylheptanoate
butyl 13-cyclopropyltridecanoate
ethyl 15-cyclopropylpentadecanoate
butyl 9-cyclopropylnonanoate
pentadecyl 7-cyclopropylheptanoate
undecyl 7-cyclopropylheptanoate
nonyl 9-cyclopropylnonanoate
heptyl 11-cyclopropylundecanoate
pentyl 13-cyclopropyltridecanoate
propyl 15-cyclopropylpentadecanoate
propyl 11-cyclopropylundecanoate
pentyl 9-cyclopropylnonate
hexadecyl 7-cyclopropylheptanoate
decyl 7-cyclopropylheptanoate

EXAMPLE 5

A. To a solution of 6.0 g. 6-cyclopropylhexanoic acid prepared from 6-bromohexanoic acid as in Example 4 in 50 ml. tetrahydrofuran at −5° under nitrogen is added dropwise 72.5 ml. of a 1 M solution of diborane in tetrahydrofuran. After the addition is completed, the reaction mixture is stirred for 1 day at room temperature. Water is then slowly added with cooling until no bubbling is observed, the reaction mixture is allowed to sit overnight, and then the tetrahydrofuran is removed by evaporation. Water and ether are added, the solution is acidified with 2N sulfuric acid and extracted with ether. The ether layer is washed in turn with saturated aqueous sodium chloride, 10% aqueous sodium hydroxide, and saturated aqueous sodium chloride, dried over calcium sulfate, filtered and the solvent removed to yield 5.02 g. 6-cyclopropylhexanol.

B. To 6.62 p-toluenesulfonyl chloride in 5.15 ml. pyridine, 15 ml. anhydrous ether and 15 ml. anhydrous methylene chloride at −15° to −10° under nitrogen is added dropwise 4.5 g. of 6-cyclopropylhexanol. The reaction mixture is stirred at −10° for 1 hour and then allowed to stand at −10° for 2 days. The mixture is added to 250 ml. ice water and ether and extracted with ether. The ether phase is acidified with cold 2N sulfuric acid until the pH is less than 7 and then washed in turn with ice water, cold 10% aqueous carbonate, ice water, cold saturated aqueous copper sulfate, ice water, and cold saturated aqueous sodium chloride. The mixture is dried over calcium sulfate, filtered, and the solvent removed by evaporation to yield 3.475 g. 6-cyclopropylhexyl p-toluenesulfonate.

C. To a solution of 9.6 g. of 6-cyclopropylhexyl p-toluenesulfonate in 120 ml. anhydrous acetone at 20°–25° is slowly added 11.0 g. lithium bromide. The reaction mixture is stirred at room temperature for 4 days, washed with acetone, filtered and the solvent removed by evaporation to yield 4.87 g. 1-bromo-6-cyclopropylhexane.

D. 0.684 g. Magnesium metal is covered with 2 ml. anhydrous tetrahydrofuran and 0.2 ml. 1,2-dibromoethane is added with stirring and heating. 1-Bromo-6-cyclopropylhexane (4.8 g.) and tetrahydrofuran (25 ml.) are added portionwise. An additional 0.207 ml. of 1,2-dibromoethane is added and the reaction mixture refluxed for 3 hours. The solution is then maintained at 24°–28° while anhydrous carbon dioxide is bubbled through it for 1½ hours. After stirring overnight under carbon dioxide, dry ether, water and 2N sulfuric acid are added until the pH is less than 7. The solution is extracted with ether and washed with water and brine, dried over calcium sulfate, filtered and the solvent removed to yield 7-cyclopropylheptanoic acid.

E. To a solution of 2.885 g. 7-cyclopropylheptanoic acid and 0.392 ml. dimethyl formamide in 20 ml. anhydrous ether is added 1.82 ml. thionyl chloride. The reaction mixture is stirred for 2 hours and then the top layer of the biphasic mixture is removed. The remaining phase is washed with anhydrous hexane, the wash solution is combined with the original upper layer and the ether and hexane are removed by evaporation.

To the resultant oil is added 20 ml. of ether and 2.14 g. decanol and 1.37 ml. pyridine is then added dropwise. The reaction mixture is stirred at 6° for 5 hours and at room temperature for 19 hours. Water (2 ml.) is added and the mixture stirred an additional 1.5 hours. The reaction mixture is then worked up as in Example 1C to yield 4.89 g. decyl 7-cyclopropylheptanoate.

A wettable powder suitable for field application after dilution can be formulated by blending and then air-milling a mixture of 20 to 30% of an ester of this invention, 60 to 70% of a solid carrier such as Attaclay X-250, 1 to 3% of an anoinic surfactant, such as Igepon T-77, and 3 to 5% of a dispersing agent such as Maras-perse N-22.

A typical formulation is as follows:

| | |
|---|---|
| Active ingredient[1] | 25.0% |
| Synthetic calcium silicate | 40.0% |
| Attapulgite Clay | 29.0% |
| Sodium lignosulfonate | 4.0% |
| Sodium N-methyl N-oleoyl taurate | 2.0% |

[1]The active ingredient is selected from one or more of the following:
decyl 7-cyclopropylheptanoate
octyl 9-cyclopropylnonanoate
methyl 11-cyclopropylundecanoate
hexyl 11-cyclopropylundecanoate The wettable powder is applied, after dilution with water, using ultra-low volume sprayers. Dilutions containing the ester within a concentration range of about 0.01% to 10% are generally employed.

The compound decyl 7-cyclopropylheptanoate can be formulated as a 25% active ingredient dust having the following composition:

| | |
|---|---|
| decyl 7-cyclopropylheptanoate | 25% |
| Synthetic Calcium Silicate | 5% |
| Attapulgite Clay | 68.5% |
| Dust Inhibitor and Sticker | 1.5% |

The mite control agents of the present invention can be used alone in an inert agriculturally acceptable carrier substance for the control of mites (Arachnids) or can be used in mixture with insecticides and/or juvenile hormone analogs known in the art to provide a broader spectrum of activity on more developmental stages of the mites or on other pestiferous insect species.

The effectiveness of the compounds of the present invention is demonstrated below.

Adults (*Tetranychus urticae*) are allowed to oviposit for 24 hours on lima bean leaf discs (diameter 1 cm.) on moist cottonwool.

After 24 hours, the adults are removed and the leaf discs are then dipped in acetone solutions of the compound being tested.

After submersion for 1 second, the solvent on the leaf discs is allowed to dry and the leaf discs are then glued to a plastic petri dish to prevent crumpling.

Six days later (when all the eggs on untreated discs have emerged), the number of unhatched eggs is calculated as a percentage of the total number originally present, corrected for any spontaneous non-emergence observed in control discs treated only with solvent (Abbott correction).

Table I presents the results of biological testing conducted as outlined above.

TABLE I

| Compound | % concentration in solution | % hatching prevented |
|---|---|---|
| methyl 11-cyclopropyl-undecanoate | 0.1 | 100 |
| decyl 7-cyclopropyl-heptanoate | 0.1 | 100 |
| octyl 9-cyclopropyl-nonanoate | 0.1 | 95 |

We claim as our invention:

1. Compounds of the formula I

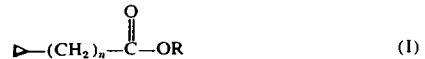

$$\triangleright\!\!-\!(CH_2)_n\!-\!\overset{\overset{\displaystyle O}{\|}}{C}\!-\!OR \qquad (I)$$

wherein $n$ is an even integer of 6 to 14 and R is alkyl of one to 16 carbon atoms, with the proviso that the total number of carbon atoms in the molecule is at least 15 but not more than 26 carbon atoms.

2. Compounds according to claim 1 wherein the total number of carbon atoms in the molecule is at least 18 but not more than 22.

3. Compounds according to claim 1 wherein R is a straight-chain alkyl.

4. Compounds according to claim 3 wherein $n$ is 6, 8, 10 or 12.

5. Compounds according to claim 2 wherein R is a straight-chain alkyl and $n$ is 6, 8, 10 or 12.

6. The compound, methyl 11-cyclopropylundecanoate.

7. The compound, decyl 7-cyclopropylheptanoate.

8. The compound, octyl 9-cyclopropylnonanoate.

9. The compound, hexyl 11-cyclopropylundecanoate.

10. A compound according to claim 5 wherein $n$ is 6 and the straight chain alkyl is octyl, nonyl, decyl, undecyl or dodecyl.

* * * * *